(12) United States Patent
Källander et al.

(10) Patent No.: US 6,849,406 B1
(45) Date of Patent: Feb. 1, 2005

(54) REVERSE TRANSCRIPTASE ASSAY KIT, USE THEREOF AND METHOD FOR ANALYSIS OF RT ACTIVITY IN BIOLOGICAL SAMPLES

(75) Inventors: Clas Källander, Uppsala (SE); Simon Gronowitz, Uppsala (SE); Ingvar Pettersson, Uppsala (SE)

(73) Assignee: Cavidi Tech AB, Uppsala (SE)

( * ) Notice: Subject to any disclaimer, the term of this patent is extended or adjusted under 35 U.S.C. 154(b) by 157 days.

(21) Appl. No.: 09/926,808

(22) PCT Filed: Jun. 16, 2000

(86) PCT No.: PCT/EP00/05563

§ 371 (c)(1),
(2), (4) Date: Dec. 21, 2001

(87) PCT Pub. No.: WO01/01129

PCT Pub. Date: Jan. 4, 2001

(30) Foreign Application Priority Data

Jun. 24, 1999 (SE) .............................. 9902410

(51) Int. Cl.[7] ................................. C12Q 1/68
(52) U.S. Cl. ............................ 435/6; 435/5; 435/91.1; 435/91.2
(58) Field of Search ................... 435/5, 6, 7.1, 91.1, 435/91.2

(56) References Cited

U.S. PATENT DOCUMENTS 5,683,875 A 11/1997 Lichtenwalter

FOREIGN PATENT DOCUMENTS

WO WO 9304199 A2 3/1993

OTHER PUBLICATIONS

Suzuki et al. Poly A–linked colorimetric microtiter plate assay for HIV reverse transcriptase. Journal of Virological Methods (1993) vol. 44, No. 2–3, pp. 189–198.*

Rasmussen et al. Covalent immobilization of DNA onto polystyrene microwells: the molecules are only bound at the 5' end. Analytical Biochemistry (Oct. 1991) vol. 198, No. 1, pp. 138–142.*

Ekstrand D. Henric L. et al., "A sensitive assay for the quantification of reverse transcriptase activity based on the use of carrier–bound template and non–radioactive–product detection, with special reference to human–immunodeficiency–virus isolation", Biotechnology and Applied Biochemistry, vol. 23, No. 2, 1996, pp. 95–105, XP000979588.

Shao X. et al., "A non–radioactive microtitre plate reverse transcriptase (RT) assay, based on immobilized template, for screening of RT activity inhibitors and evaluation of the mode of action", Antiviral Chemistry & Chemotherapy, vol. 8, No. 2, 1997, pp. 149–159, XP000981902.

Awad Raymond J –K. et al., "Measurement of levels of human immunodeficiency virus type 1 reverse transcriptase (RT) and RT activity–blocking antibody in human serum by a new standardized colorimetric assay", Journal of Clinical Microbiology, vol. 35, No. 5, 1997, pp. 1080–1089, XP002159505.

Database WPI, Week 0014, Derwent Publications Ltd., London, GB; AN 1992–223246, "Reverse transciptase determ.–by using hybridized substance of solidified primer and template RNA", XP002159753 & JP 04 148698 A (Toyo Jozo KK), May 21, 1992.

Kazuo Suzuki et al., "Poly A–linked colorimetric microtiter plate assay for HIV reverse transcriptase", p. 189–p. 198, Journal of Virological Methods, vol. 44, 1993.

Tomas Porstmann et al., "A sensitive non–isotopic assay specific for HIV–1 associated reverse transcriptase", p. 181–p. 188, Journal of Virological Methods, vol. 31, 1991.

* cited by examiner

*Primary Examiner*—Ulrike Winkler
(74) *Attorney, Agent, or Firm*—Bacon & Thomas (57) ABSTRACT

A reverse transcriptase (RT) assay kit for analysis of RT activity in biological samples is described. The kit comprises solid phase bound prA and/or pdA template(s) obtainable by contacting a polystyrene-based solid phase with a 1-methylimidazole-containing coupling solution, and RT-type adapted assay components selected from a buffer, divalent metal ion, chelator, polyamine, RNase inhibitor, reducing agent, salt, stabilizing agent, and detergent, and deoxynucleotide triphosphate, primer, protective agent and concentrated washing buffer, and optionally lyophilized reference enzyme(s), and further optionally lyophilized alkaline phosphatase conjugated anti-BrdU monoclonal antibody, alkaline phosphatase substrate buffer and alkaline phosphatase substrate, and written instructions for use of the assay kit. Further, a method and a use of the assay kit for the qualitative and quantitative analysis of RT activity in a biological sample, optionally followed by evaluation of the status of a RT activity related disorder or disease based on the result of the analysis of the RT activity, are disclosed.

14 Claims, 4 Drawing Sheets

REVERSE TRANSCRIPTASE ASSAY KIT, USE THEREOF AND METHOD FOR ANALYSIS OF RT ACTIVITY IN BIOLOGICAL SAMPLES

This application is a 371 of International Application PCT/EP00/05563, filed 16 Jun. 2000, of which the entire disclosure of the pending, prior application (which was published in English) is hereby incorporated by reference.

The present invention relates to a reverse transcriptase (RT) assay kit for analysis of RT activity in biological samples. The invention also relates to a method and a use of the RT assay kit for the qualitative and quantitative analysis of RT activity in a biological sample, optionally followed by evaluation of the status of a RT activity related disorder or disease based on the result of the analysis of the RT activity.

BACKGROUND OF THE INVENTION

Reverse transcriptase (RT) is the crucial enzyme responsible for the synthesis of DNA from viral RNA for all retroviruses, including human immunodeficency virus (HIV) (Baltimore—70, Temin—70, Barre-Sinoussi et al—83). This process involves three different enzymatic activities: synthesis of the first DNA strand, degradation of the viral RNA strand in the DNA/RNA hybrid, and synthesis of the second DNA strand (for a review see Goff).

Retroviruses can exist either in exogenous or endogenous forms or both. The main difference is that an endogenous retrovirus has entered the germline and thus its DNA is present in all cells of the organism, in contrast to an exogenous retrovirus which is only able to enter cells with the appropriate receptor for that specific virus. Endogenous retroviruses (ERVs) in humans are called HERVs. The integrated proviral form of an endogenous retrovirus has the same fundamental structure as that of an exogenous retrovirus. The integration of some HERVs into the germline is thought to have occurred 35 to 45 million years ago. These retroviral sequences constitute 1% of the mammalian genome and hence also of the human genome. Thus, they are present in all human cells and inherited according to ordinary Mendelian laws.

Many families of HERVs are present in the human genome. The copy number per haploid human genome of HERVs varies between a single copy to thousands of copies for different families. The highest nucleotide sequence conservation is found in the pol gene. This feature has been used to derive relationship between HERV families. Although many of the HERVs and their ORFs are defective, mRNA transcripts have been detected from most HERV families in several tissue-types (reviewed in Wilkinson et al 1994, Leib-Mösch and Seifarth 1996). In addition, virion particles with polymerase and protease activity have been observed in normal human placentas, oocytes, teratocarcinomas, mammary carcinoma tissues and in salivary glands of some autoimmune patients (reviewed in Wilkinson et al. 1994, Urnovitz and Murphy 1996, Tönjes et al., 1997). Stress conditions like anoxia and UV irradiation might also induce the expression of HERVs as been observed for infectious retroviruses (reviewed by Duvic 1995).

Several HERVs have been localized to chromosomal breakpoints within the genome (Di Cristofano et al. 1995, Meese et al. 1996). Recombination between HERV sequences located at different chromosomal sites may cause genomic rearrangements including translocations, inversions, duplications and deletions. Such recombinatorial events are responsible for generating genomic instability that is an important feature of evolution. In addition, many tumors are characterised by specific genomic rearrangements thought to play a crucial role in the tumorogenesis. The relationship between presence of infectious retroviruses and development of tumors in the host suggests that HERVs are associated with cancer. Virion particles and retrovirus related antigens are frequently observed in primary tumor samples also in the absence of infectious viruses (Weiss 1984, Faff et al. 1992). In addition, antibodies directed to retroviral proteins have been demonstrated in the sera of patients with cancer (Weiss 1984). Moreover, HERV sequences are found to be highly expressed in certain tumor derived cell lines (reviewed in Löwer et al. (1996).

Endogenous proviruses can also recombine with exogenous variants (Martinelli et al. 1990). Novel recombinants receive an altered phenotype. This might contribute to the rapid evolution of new infectious retroviruses. The env gene is mainly affected since mutations in other parts may be deleterious and not compatible with particle formation. Some retroviral strains are found to be symbiotic in one species and pathogenic in another. These findings indicate a severe problem in xenotransplantations. Symbiotic ERVs provided by the transplanted tissues could be pathogenic in the new host. They might be able to interact with cell surface receptors needed for retroviral fusion present on cells of the new host. In addition, recombination with endogenous retroviral sequences within the genome of the tissue recipient can occur and create new infectious retroviruses that might spread in the population. Both endogenous and exogenous retroviruses can contribute to vertical and horizontal transmission of genetic material within and between species and provide mechanisms for evolution of new pathogenic agents.

Both infectious retroviruses and ERVs have been found to exhibit immuno regulatory functions (reviewed in Krieg et al. 1992). These effects have mainly been studied in mice but there are some observations that support existence of similar mechanisms for HERVs. If HERV sequences can deregulate an immune response they can cause autoimmune diseases. These effects could be directly modulated by HERV proteins or indirectly by influencing the expression of molecules involved in the immune response. HERV proteins can be exposed on the cell surface. Loss of self tolerance towards these protein sequences could cause autoimmune reactions against cells exposing them. Antibodies produced following retroviral infection might be crossreactive with HERV encoded proteins and responsible for loss of tolerance. This phenomenon has been observed in transgenic mice (Zinkernagel et al. 1990). In addition, loss of tolerance to ERV encoded env proteins was observed in mice that spontaneously developed an autoimmune glomerulonephritis (reviewed in Krieg et al. 1990 and 1992). Some observations in humans might support existence of crossreactive antibodies between endogenous and exogenous retroviral proteins. Antibodies against retroviral proteins have been detected in sera of autoimmune patients (reviewed in Krieg et al. 1992, Urnovitz and Murphy 1996). In certain cases, the sera were found to react also with exogenous retroviruses. Retroviral infections have been associated with the onset of autoimmune diseases (reviewed in Krieg et al. 1990 and 1992). Moreover, infectious retroviral proteins show partial similarity to self antigens that are frequent targets for autoantibodies (reviewed in Krieg et a 1992). They could trigger autoimmune responses towards such targets, a mechanism referred to as molecular mimicry. However, similarities of HERV proteins to known self antigens have not yet been detected.

Assays for RT activity have become accepted techniques for the detection and quantification of retroviruses in cell cultures. They are together with p24 antigen assays used as confirmatory tests for HIV isolation (Jackson—88, Gupta—87). RT is also one of the main targets in the attempt to find efficient antivirals against HIV. A conventional RT activity assay is performed by utilizing a soluble enzyme assay with an artificial template-primer construction and tritiated deoxynucleotide triphosphate as nucleotide substrate (Baltimore-71, Lee et al—87). This early system was based on detection of incorporation of radioactivity into trichloroacetic-acid (TCA) precipitable RNA/DNA hybrids. Use of beta emitting nucleotides requires the use of scintillation fluids for detection of radioactivity, which often results in poor reproducibility due to quenching problems. This method is relatively cumbersome and not easily adapted to large scale screening of large numbers of samples. It is also very sensitive to the effects of disturbing factors in the samples.

During the last decade of intensive research on HIV, the RT assay has been improved using different techniques. The introduction of $I^{125}$ labeled substrate gave an increased sensitivity and eliminated quenching and the use of scintillation fluids (Neumüller et al—90). The introduction of templates or primers linked to solid phases simplified the separation between substrate and product, eliminated the need of TCA precipitations and resulted in a "one tube RT assay" (Gronowitz et al—90, EP 0 447 442 B1).

More recently the use of radioactivity as label in RT assay has been eliminated by the use of modified nucleotide bases containing either antigenic eptiopes or structures with high affinity to defined ligands. The presence of these epitopes or structures in the newly synthesized RNA/DNA hybrid is then used for binding of antibodies or ligands conjugated with e.g. ELISA enzymes. The amount of ELISA enzymes bound is then determined in a secondary enzyme assay.

Porstmann et al 1991 utilizes 5-bromo-deoxyuridine (BrdU) triphosphate as nucleotide substrate in RT assay. The amount of BrdUMP incorporated is in a secondary step determined in an immunoassay using alkaline phosphatase conjugated monoclonal anti-BrdU antibodies.

Eberle and R. Scibl 1992 measure the incorporation of digoxigenin labeled dUTP into newly synthesized DNA instead of radioactively labeled dTTP. To be able to perform the separation of non-incorporated nucleotides from the newly synthesized DNA, biotin labeled dUTP is also added to the reaction mixture. After reverse transcription, the newly synthesized double labeled DNA is immobilized on streptavidin coated ELISA wells and evaluated photometrically by binding of peroxidase-conjugated anti-digoxigenin-antibodies. This procedure has been the base for a kit RT-assay which is commercially available from Boehringer Mannheim.

Urabe et al 1994 has developed a non-radioactive RT-assay based on incorporation of biotin-dUTP in an immobilized odT/prA construct. The amount of incorporated nucleotide substrate is measured photometrically after addition of streptavidin conjugated alkaline phosphatase. Closest prior aft to the current invention was developed by Ekstrand et al 1996. In that assay poly (rA) covalently bound to the wells of a 96 well microtiter plate serves as template for the incorporation of BrdUMP during the reverse transcription step. The amount of BrdUMP incorporated into DNA is then determined immunologically according to a similar procedure as used by Porstmann et al 1991. The method is available as RT determination kits from Cavidi Tech, Uppsala, Sweden.

Another principle for detection of RT-activity, commercially exploited by NEN (New England Nuclear, USA), is utilization of sequence specific probes for detection of newly synthesized cDNA. The enzymatic reaction utilizes a heteropolymeric RNA molecule with a 20-base oligonucleotide primer complementary to the RNA sequences near the 5'-end. A complete cDNA strand is produced during the RT-reaction. After hydrolysis of the template RNA the cDNA is hybridized with two different oligonucleotide probes, the capture and the detection probe. The capture probe is used for binding the cDNA to a microplate well. The detection probe is conjugated to horseradish peroxidase, which after washing to remove unused nucleotide substrate and free probes gives a color reaction.

The detection sensitivity in the last type of assay can be increased by polymerase chain reaction amplification of the cDNA produced by the RT reaction. The amplified DNA can thereafter be detected with different types of labeled probes (Silver 93, Heneine 1995, U.S. Pat. Nos. 5,817,457, 5,849, 494).

For some applications of the knowledge of RT activity in biological samples it is desirable to use a RT assay giving quantitative results. Such applications comprise disease or disorder monitoring where RT assay results from measurements made at different times are to compared, and diagnosing of diseases or disorders where the level of RT activity compared to standard levels indicates if the patient is at risk or in deed is suffering from the disease or disorder in question.

In some instances it is desirable to use an assay which is as sensitive as possible, i.e. is able to measure as small amounts of RT activity as possible, in biological samples, so that the presence and magnitude of RT activity can be related to disorders and diseases at an early stage.

DESCRIPTION OF THE INVENTION

The present invention provides an RT assay which is easy to use for screening purposes and which is very sensitive for RT activity.

More precisely, the present invention is directed to a reverse transcriptase (RT) assay kit which comprises one or several package(s) containing solid phase bound polyriboadenylic acid (prA) and/or polydeoxyadenylic acid (pdA) template(s) obtainable by contacting a polystyrene-based solid phase with a coupling solution comprising 1-methylimidazole, and prA and/or pdA, followed by incubation, washing with a wash buffer, drying and packaging. The kit comprises also RT-type adapted separately packaged assay components selected from the group consisting of a mixture of or separately a buffer, pH-≅7–8, divalent metal ion, chelator, polyamine, RNase inhibitor, reducing agent, salt, stabilizing agent, and detergent, and a mixture of or separately lyophilized deoxynucleotide triphosphate, primer, protective agent and concentrated washing buffer, and written instructions for use of the assay kit. Optionally the kit comprises lyophilized reference enzyme(s). Optionally, the kit further comprises components of a detection system comprising lyophilized alkaline phosphatase conjugated anti-BrdU monoclonal antibody, alkaline phosphatase substrate buffer and alkaline phosphatase substrate, such as pNPP tablets.

In a preferred embodiment of the RT assay kit according to the invention, the solid phase is a microtiter plate, and an aliquot of the coupling solution, which comprises 100 mM 1-methylimidazole, pH≅5–7, and 0.5–2 mg/ml prA and/or pdA, is added to each well, followed by the incubation at a temperature of 10–60° C. for 0.5–10 h, and washing each well for the removal of the 1-methylimidazole with the wash buffer, which comprises Bis-Tris propane, pH≅5–7.

In a particularly preferred embodiment of the RT assay kit according to the invention, 100 µl of the coupling solution, which comprises 100 mM 1-methylimidazole, pH≅6.25, and 1 mg/ml prA and/or pdA, is added to each well, followed by the incubation at room temperature for ≅2 h, washing of each well with 2×300 µl of the wash buffer, which comprises 10 mM Bis-Tris propane, pH≅6.25, drying the plates at 37° C. for ≅25 minutes and putting the plates in foil bags and vacuum sealing the bags.

In a further embodiment of the RT assay kit according to the invention, the assay components are selected from the group consisting of the buffers Tris and Hepes, pH≅7–8, the divalent metal ions $Mg^{2+}$ and $Mn^{2+}$, the chelators ethylene-diaminetetraacetic acid (EDTA) and ethylene glycol-bis(β-aminoethyl ether) N,N,N',N'-tetraacetic acid (EGTA) and, the polyamines spermine and spermidine, the RNase inhibitors heparin sulfate and dextran sulfate, the reducing agents dithiothretiol (DTT), dithioerythritol (DTE), and glutathione, the salts NaCl and KCl, the stabilizing agents newborn calf serum (NCS) and bovine serum albumin BSA, the detergents Tween 20 and Triton X-100, the deoxynucleotide triphosphate BrdUTP, the primer oligo dT or oligo dN where N is another T analog such as U, and the protective agents ATP, GTP and CTP.

The present invention is also directed to the use of an assay kit according to the invention for the qualitative and quantitative analysis of RT activity in a biological sample, e.g. a biological sample which is selected from cell extracts and biological fluids, such as plasma, serum, spinal fluid, synovial fluid and pleural fluid.

In a preferred embodiment the use according to the invention is followed by valuation of the status of a RT activity related disorder or disease based on the result of the analysis of the RT activity.

Additionally, the present invention is directed to a method of qualitative and quantitative analysis of RT activity in a biological sample comprising the steps of using and following the written instructions for the RT assay kit according to the invention for the determination of the RT activity in the biological sample, e.g. a biological sample which is selected from cell extracts and biological fluids, such as plasma, serum, spinal fluid, synovial fluid and pleural fluid.

In a preferred embodiment the method according to the invention is followed by evaluation of the status of a RT activity related disorder or disease based on the result of the analysis of the RT activity.

The present invention will now be illustrated by reference to the drawings and a more detailed description of embodiments, but these embodiments should not be considered as limiting to the scope of protection defined in the appended claims.

SHORT DESCRIPTION OF THE DRAWINGS

FIG. 5. The RT activity in a A) medium of a culture of HTLV 1 transformed cells and a B) medium from a BLV infected culture were determined with two methods. The absorbance values obtained were plotted against the amount of sample added to the reaction mixture.

DETAILED DESCRIPTION OF EMBODIMENTS OF THE INVENTION

The RT assay kit of the invention comprises three different types of components, namely
1) A template consisting of polyriboadenylic acid (prA) or polydeoxyadenylic acid (pdA) attached to a solid phase.
2) Reaction mixtures that allow the enzymes to polymerise a new DNA strand in a primer-dependent manner using the attached template polynucleotide.
3) Components of a detection system for the immunological detection of the in vitro synthesized DNA strand.
1) Solid Phase Bound Template A method has been developed whereby prA or pdA can be attached to certain types of microtiter plates in a manner that allows the polynucleotides to serve as templates for primer-dependent dNTP incorporation by viral and cellular RNA- and DNA-dependent DNA polymerases (reverse transcriptases, RTs). It has been shown to work on two commercially available microtiterplates, CovaLink™ and NucleoLink™ from Nalge Nunc International. The prA coupled microtiter plates used for the assay kits according to the invention are produced from NucleoLink™ strips. The procedure and the buffers are described in Table 1. The mechanism of the binding is not known as the procedure does not correspond to methods recommended or suggested by the manufacturer or is explicitly stated in the literature. A possible reaction mechanism involves reactive groups introduced during the manufacturing procedure but other than those grafted on for the known and intended use of that specific surface. Similar results are expected to be obtained with other polystyrene-based microtiter plates from other commercial sources. A method for chemically activating polystyrene to get a surface with properties equal to those of the CovaLink™ plates has been published (Zammatteo et al—96). Several other methods for attaching polynucleotides to plastic surfaces have also been published (Zammatteo et al—96, Gregorius et at—95, Niveleau et al—93, Rasmussen et al—91, Ghosh and Musso—87).
2) RT Type Adapted Reaction Mixtures The general conditions for obtaining nucleotide incorporation by RNA- and DNA-dependent DNA polymerases in soluble systems using purified enzymes are simple and well known. They include a buffer keeping the pH around 7.5, a divalent metal ion, $Mg^{2+}$ or occasionally $Mn^{2+}$, a salt to adjust the ionic strength, for some enzymes a reducing agent and a bit of detergent. Provided with this simple reaction buffer the enzymes will be able to utilize added template, primer and deoxynucleotide triphosphates to synthesize a DNA strand. This general concept takes no account of the differences in optimal or especially adapted reaction conditions that are required between different classes or types of reverse transcriptases. Another important aspect is the desired ability of the reaction mixture to tolerate addition of untreated biological fluids or cell extracts as the source of the RT enzymatic activity.

Systematic testing using both crude samples such as cell culture supernatants and purified enzymes revealed other reaction components that were used to create reaction mixtures optimized or especially adapted for specific reverse transcriptases.

Table 2 contains a summary of the components used to compose the individual RT type adapted reaction mixtures. The compositions of typical reaction mixtures are presented in Table 3.

The reverse transcriptase assay method of the invention is performed as described below. The first step in the assay is to add 100 µl of reaction mixture to each well of the prA-coupled microtiter plate, followed by a 20–60 min pre-incubation at 33° C. The sample containing the reverse transcriptase is then added in 50 µl of buffer, giving a final assay volume of 150 µl, and the microtiter plate is then incubated at 33° C. Each sample is added to duplicate microtiter plates to allow for two assay times, standarized to 3 hours and overnight, meaning 16–20 hours. A step-by-step procedure is provided in the written instructions or user's manual included with each kit. It contains suggestions or instructions on how to adapt the generic reverse transcriptase assay components for some or all of the following applications: 1) Quantification of RT activity. 2) Screening of RT activity in cell extracts, cell supernatants and/or biological fluids including but not limited to plasma, serum, spinal fluid, synovial fluid and pleural fluid. 3) Determination of RT activity blocking antibody. 4) Determination of $IC_{50}$ values of RT activity inhibiting substances.

Using these reaction mixtures and the solid phase bound templates we designed the claimed assays which were either more sensitive in direct measurements of RT activity than other previously described assays based on solid phase bound templates or allowed detection of previously unknown reverse transcriptase activities.

3. Immunological Detection of the In Vitro Synthesized DNA Strand.

The polymerase in the sample synthesizes a DNA strand using the Bromo-deoxyuridine triphosphate (BrdUTP) provided in the reaction mixture.

The incorporated BrdUMP is detected by a BrdU binding monoclonal antibody conjugated to alkaline phosphatase. The alkaline phosphatase activity of the bound antibody is then quantified by adding a substrate solution-containing para-nitro phenyl phosphate, pNPP. The substrate solution turns yellow when the pNPP is cleaved by the alkaline phosphatase. The optical density (OD) is measured in a standard ELISA reader at a wavelength of 405 nm. The OD value corrected for background is proportional to the RT activity in the sample.

The detection step is performed as described below. A step-by-step procedure is provided in the written instructions or user's manual included with each kit. The compositions of the buffer solutions are given in table 4.

After the reverse transcriptase assay, the microtiter plate is washed either using one of the commercially available ELISA plate washers or by serially immersing the plate in buckets with the washing buffer. The conjugated antibody is optionally provided in the kit in lyophilized form. After reconstitution with 1% triton X-100 in double distilled water 100 µl of the antibody solution is added to each well and the microtiter plate is incubated at 33° C. for 90 minutes. To remove excess antibody, the plate is subsequently washed in the same manner a second time. The substrate solution is prepared from buffer and pNPP tablets optionally provided with the kit. The OD values are then measured at suitable time intervals.

The linear relationship between amount of alkaline phosphatase enzyme bound and the concentration of the yellow product breaks down at high OD values. By measuring the OD at different times it is possible to get useful values, i.e. OD values within the linear reading range of the particular instrument, for samples with both high and low amounts of product formed during the reverse transcriptase assay step. The reference RT enzymes optionally included in some but not all of the kits are calibrated to give titration curves with useful OD values when the OD is measured after 30 min, 2 hours and 16–20 hours, i.e. overnight.

The improved performance obtained with the RT assay kits of the invention is demonstrated in Table 5. HIV-1 RT titration curves were obtained with the previously known Lenti RT kit from Cavidi Tech AB and with an assay kit of the present invention. The OD values can be plotted against the RT enzyme concentration and fitted to a straight line using least squares fit. The k values in Table 6 are the slopes of the calculated straight lines and are a measure of the sensitivity of the assay. It can be seen that the assay kits of the invention have k-values that are an order of magnitude higher. In practical terms this translates to useful measurements from samples containing a much lower concentration of HIV-1 reverse transcriptase and/or to time-saving. Shorter reverse transcriptase assay times and/or a shorter alkaline phosphatase reading time means shorter turn-around time for users of the kits of the resent invention.

Typical Components of the Kit of the Invention

A. Two 96-well microtitre plates with prA and/or pdA attached.
B. A sample dilution and reaction buffer containing a RT type adapted mixture of components I–IX listed in Table 2.
C. Lyophilized reaction components X–XII mixed or provided in separate vials.
D. Lyophilized reference enzyme either recombinant, purified natural or viral particles.
E. Concentrated Washing Buffer
F. Lyophilized alkaline phosphatase conjugated anti-BrdU monoclonal antibody, denoted "RT Product Tracer"
G. Alkaline phosphatase substrate buffer and pNPP tablets
H. Written instructions or Manual

EXAMPLES

Example 1

Improved Detection of PERV (Porcine Endogenous Retrovirus) RT in Cell Supernatants.

Figure 1:
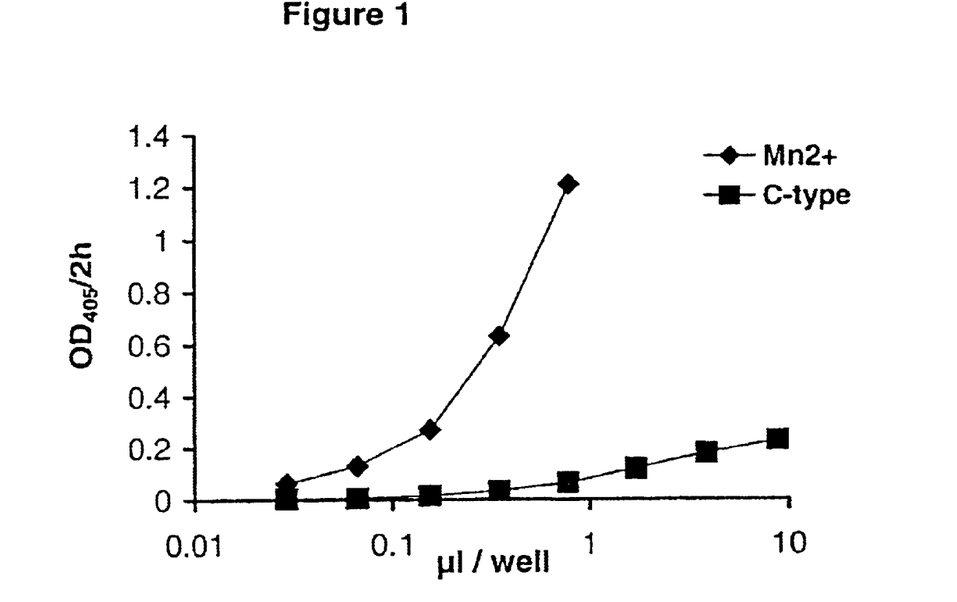
FIG. 1. The RT activity was determined in a medium from a culture of the PK 15 cell line with two methods. The absorbance values obtained were plotted against the amount of media added to the reaction mixture.

The porcine cell line PK-15 (porcine kidney) is known to continuously produce small amounts of PERV. Supernatants from a culture of PK-15 cells were serially diluted. The capacity of the C-type RT assay of Cavidi tech AB and the $Mn^{2+}$ assay of the current invention to detect RT activity at each dilution were tested. The data shown in FIG. 1 originate from an over-night-RT assay.

The assay kit of the invention exhibits an approximately 25 times increased sensitivity compared to the one of previous art. It was not possible to use more sample to compensate for the difference in detection sensitivity, since the C-type assay suffered from increased background levels and deviations from linearity with time and/or sample amount at higher supernatant concentrations (>2 µl/well).

The assay kit of the invention can be used in studies regarding the possible transfer of exogenous retrovirus and/ or activation of endogenous retrovirus in conjunction with xenotransplantation.

Example 2
Direct Measurement of Reverse Transcriptase in Synovial Fluids.

Recent DNA hybridization experiments have suggested the association between certain rheumatic disorders and the presence of retrovirus associated sequences. Frozen samples of synovial fluids from patients with rhematoid arthritis were obtained from the department of Rheumatology at Karolinska sjukhuset, Stockholm, Sweden. The samples had been cleared from cells and debris by low speed centrifugation before freezing. The samples were thawed, serially diluted and investigated for RT activity.

Figure 2:
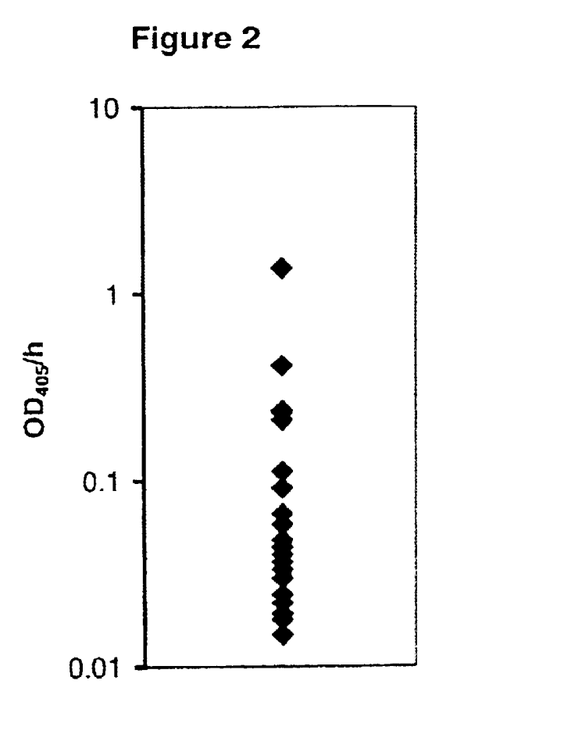
FIG. 2. Direct RT determination in synovial fluid samples collected from patients suffering from rheumatoid arthritis. The values plotted were obtained from 1 µl samples and an over-night RT reaction.

The activities obtained were recalculated to $OD_{405}/h$. FIG. 2 presents the RT activities found using 1 µl sample and an over-night enzyme reaction in the synovial fluid RT assay of the invention. No RT activity was detected in any of the investigated samples by the Lenti or C-type RT assay of Cavidi Tech AB.

Example 3
Detection of RT Activity in Extracts from Human Breast Cancer.

An exogenous or endogenous human counterpart to the (mouse mammary tumor virus) MMTV has been implicated in the etiology of human breast cancer. Using recombinant MMTV RT to optimize the assay conditions, RT activity could be detected in extracts from breast cancers without prior concentration or purification. Frozen extracts from human breast cancers were obtained from the department of Oncology at Akademiska sjuhuset, Uppsala, Sweden. The tumor tissue had been homogenized and suspended in a standard buffer (pH 7.4). Supernatants were collected after clarification by low speed centrifugation. The samples were thawed, serially diluted and investigated for presence of RT activity in the $Mg^{2+}$ RT assay of the invention and the Lenti or C-type RT assay of Cavidi Tech AB.

Figure 3:
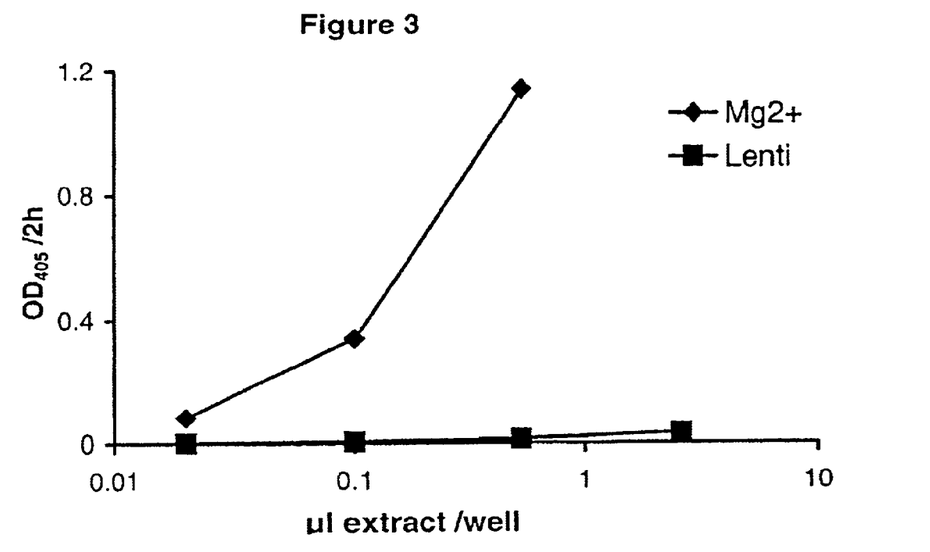
FIG. 3. The RT activity was determined in an extract from a breast cancer with two methods. The absorbance values obtained are plotted against the amount of extract added to the reaction mixture.

FIG. 3 shows a representative example of the results obtained using an over-night RT reaction combined with 2 hours AP reaction. The difference in detection sensitivity between the $Mg^{2+}$ RT assay of the invention and the Lenti RT assay of Cavidi Tech AB was approximately 400 times. No activity was detected in the C-type RT assay of Cavidi Tech AB.

Figure 4:
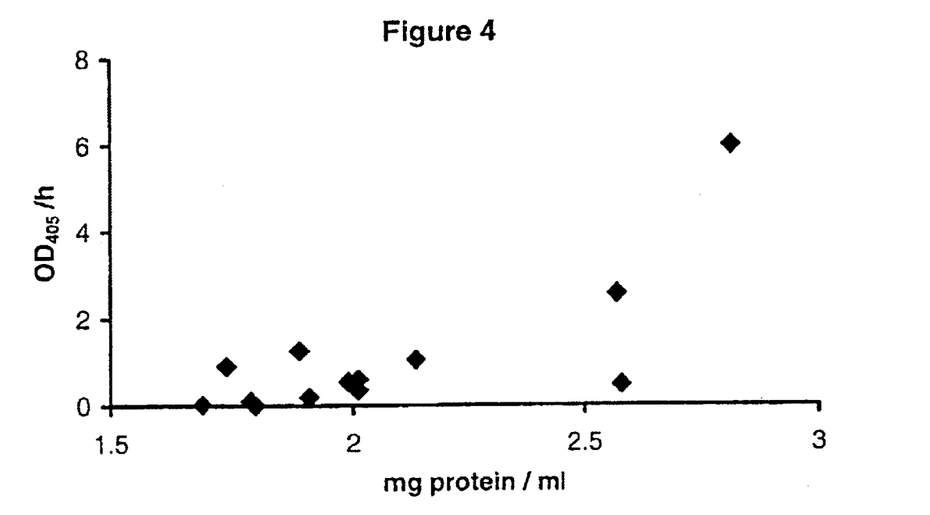
FIG. 4. Direct determination of RT activity in extracts from breast cancer biopsies. The absorbance values plotted against the protein concentration in each sample were obtained from 1 µl extract and an over-night RT reaction.

FIG. 4 Illustrates the variation of the RT activities detected by the $Mg^{2+}$ RT assay in tumor extracts from different patients.

The assay kit of the invention can be used in studies regarding the possible role of exogenous or endogenous retroviruses in the etiology of breast cancer as well as be used for diagnostic purposes.

Example 4
Detection of (Human T-cells Leukemia Virus) HTLV like Viruses in Supernatants from Cell Cultures.

Some HTLV infected individuals go on to develop oncological or Myelopathic disorders. In certain parts of Japan and South Asia the associated disease adult T-cell leukemia was first described. A neurological disorder, tropical spastic paraparesis, was initially described in patients from the Caribbean. Methods capable of detecting exposure to the virus and/or the continued presence of low levels viral activity is desirable.

A highly related bovine virus, bovine leukemia virus (BLV) is a pathogen in cows with great economic consequences for the dairy and cattle breeding industries. BLV was used to optimize an assay for BLV/HTLV RT activity.

Figure 5:
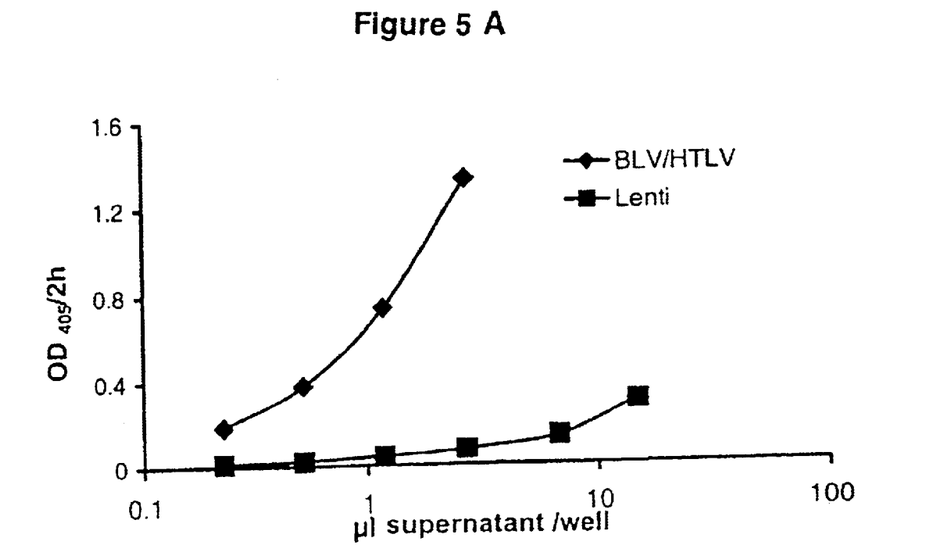

FIG. 5A illustrates the difference in detection sensitivity between the assay kit of the invention and the Lenti RT assay of Cavidi Tech AB. Cell culture supernatants from the HTLV 1 transformed cell line MT-2 were serially diluted and the two RT assays were used to determine the amount of RT activity in each sample. The RT reaction time used was over-night (14 hours).

FIG. 5B shows the corresponding data from a dilution set of supernatants from FLK-BLV cells. (This cell line is chronically infected by BLV).

The total gain in detection sensitivity was approximately 25 fold for the HTLV enzyme and 30-fold for the BLV enzyme, respectively. The increase in sensitivity was essential to obtain a significant signal from the supernatant of the MT-2 cells.

Example 5

Direct Determination of RT Activity in Crude Sera from SIV Infected Macaques.

Quantification of RT activity in serum can be used for detection of virus replication during acute lenti virus infection. The serum RT activity is later, quenched by the production of RT inhibitory antibody.

Figure 6:
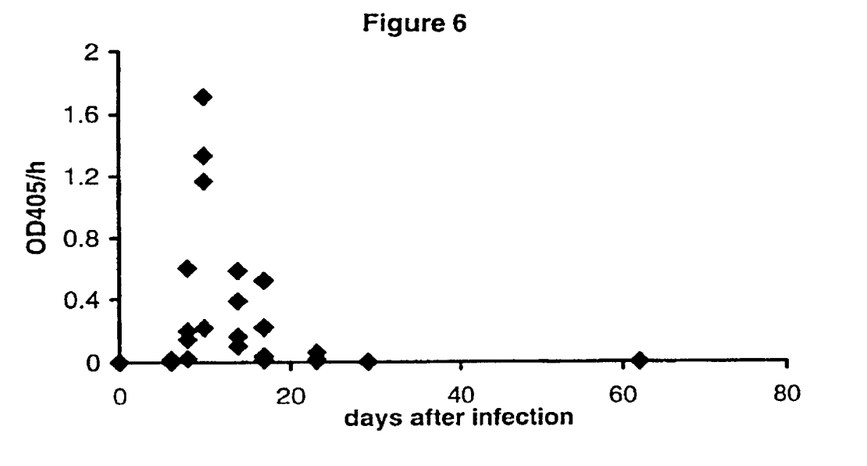
FIG. 6. Direct determination of RT activity in serum from SIV infected macaques. The absorbance values obtained in a 4-hour RT assay were plotted against serum sampling day.

A group of four cynomolgus macaques (*Macaca fascicularis*) engaged as untreated controls in a treatment study were infected with ten monkey infectious doses (MID50) of SIVsm. Serum sampled at indicated times after infection was serially diluted and assayed for RT activity utilizing the Lenti RT assay of the invention. Five µl serum samples were included in a four hours RT reaction and the absorbance values obtained were recalculated into $OD_{405}/h$ and plotted against days after infection, see FIG. 6.

The Lenti RT assay of the invention is sensitive enough to detect virus replication by analysis of serum sampled during acute stage infection. The tests currently used for screening for HIV positivity among human blood donors is based on detection of antibodies towards HIV-1 proteins and fail to detect infected persons during the acute stage of the infection. These tests are in some countries supplemented by detection of viral antigen by ELISA or viral genome by PCR. Both types of tests may fail to detect deviant virus strains and immunological variation among HIV viruses. RT has an or the replication of all retroviruses and the current assay offers an detection of acute infections.

TABLE 1

Procedure for producing prA coated NucleoLink ™ microtiter plates

| Coupling solution | 100 mM | 1-methylimidazole pH 6.25 |
|---|---|---|
|  | 1 mg/ml | polyriboadenylic acid |
| Wash buffer | 10 mM | Bis-Tris Propane pH 6.25 |

Add 100 µl coupling solution to each well.
Incubate plates at room temperature for 2 h.
Wash each well with 2×300 µl wash buffer.
Dry the plates at 37° C. for 25 minutes.
Put the plates in foil bags and vacuum seal them.
Store at −20° C.

TABLE 2

Components used to compose RT type adapted reverse transcriptase assays

| | Component | Substance | Useful concentration range in final reaction mixture |
|---|---|---|---|
| I | Buffer | Tris, Hepes | 10–100 mM; pH 7.0–8.0 |
| II | Divalent metal ion | Mg2+, Mn2+ | 0–20 mM |
| III | Chelator | EDTA, EGTA | 0–0.5 mM |
| IV | Polyamine | Spermine, Spermidine | 0–20 mM |
| V | RNase inhibitor | Heparin sulfate, Dextran sulfate | 0–100 µg/ml |
| VI | Reducing agent | DTT, DTE, Glutathione | 0–5 mM |
| VII | Salt | NaCl, KCl | 0–100 mM |
| VIII | Stabilising agent | NCS, BSA | 0–1 mg/ml |
| IX | Detergent | Tween 20, Triton X-100 | 0–1.0% |
| X | Deoxynucleotide triphosphate | BrdUTP | 1–50 µM |
| XI | Primer | oligo dT | 5–100 ng/ml |
| XII | Protective agent | ATP, GTP, CTP | 0–5 mM |

Abbreviations:
EDTA Ethylenediaminetetraacetic Acid
EGTA ethylene glycol-bis(β-aminoethyl ether) N,N,N',N'-tetraacetic acid
DTT Dithiothretiol
DTE Dithioerythritol
NCS Newborn Calf serum
BSA Bovine serum albumin

TABLE 3

| | Component | Substance | Concentration in final reaction mixture |
|---|---|---|---|
| Components in optimized Lenti reverse transcriptase assay of the invention ||||
| I | Buffer | Hepes-HCl | 10 mM; pH 7.6 |
| II | Divalent metal ion | MgCl$_2$ | 4 mM |
| III | Chelator | EGTA | 0.2 mM |
| IV | Polyamine | Spermine | 2 mM |
| V | RNase inhibitor | Dextran sulfate | 50 µg/ml |
| VI | Reducing agent | | |
| VII | Salt | | |
| VIII | Stabilising agent | BSA | 0.5 mg/ml |
| IX | Detergent | Triton X-100 | 0.5% |
| X | Deoxynucleotide triphosphate | BrdUTP | 16 µM |
| XI | Primer | oligo dT | 80 ng/ml |
| XII | Protective agent | GTP | 0.5 mM |
| | Preservative | NaN$_3$ | 1.92 mM |
| Components in optimized BLV/HTLV reverse transcriptase assay of the invention ||||
| I | Buffer | Hepes-HCl | 10 mM; pH 7.8 |
| II | Divalent metal ion | MgCl$_2$ | 8 mM |
| III | Chelator | EGTA | 0.2 mM |
| IV | Polyamine | Spermidine | 1 mM |
| V | RNase inhibitor | Dextran sulfate | 2 µg/ml |
| VI | Reducing agent | Glutathione | 0.6 mM |
| VII | Salt | | |
| VIII | Stabilising agent | BSA | 0.5 mg/ml |
| | | NCS | 0.5% |
| IX | Detergent | Triton X-100 | 0.5% |
| X | Deoxynucleotide triphosphate | BrdUTP | 16 µM |
| XI | Primer | oligo dT | 80 ng/ml |
| XII | Protective agent | GTP | 0.5 mM |
| | Preservative | NaN$_3$ | 1.92 mM |
| Components in optimized Mg$^{2+}$ reverse transcriptase assay of the invention ||||
| I | Buffer | Hepes-HCl | 10 mM; pH 7.6 |
| II | Divalent metal ion | MgCl$_2$ | 25 mM |
| III | Chelator | EGTA | 2.5 mM |
| IV | Polyamine | Spermine | 0.15 mM |
| | | Spermidine | 3 mM |
| V | RNase inhibitor | | |
| VI | Reducing agent | Glutathione | 1 mM |
| VII | Salt | | |
| VIII | Stabilising agent | BSA | 0.5 mg/ml |
| | | NCS | 0.25% |
| IX | Detergent | Triton X-100 | 0.5% |
| X | Deoxynucleotide triphosphate | BrdUTP | 16 µM |
| XI | Primer | oligo dT | 80 ng, ml |
| XII | Protective agent | ATP, GTP | 0.5 mM |
| | Preservative | NaN$_3$ | 1.92 mM |
| Components in optimized Mn2+ reverse transcriptase assay of the invention ||||
| I | Buffer | Hepes-HCl | 10 mM; pH 7.5 |
| II | Divalent metal ion | MnCl$_2$ | 6 mM |
| III | Chelator | EDTA | 0.3 mM |
| IV | Polyamine | Spermidine | 12 mM |
| V | RNase inhibitor | | |
| VI | Reducing agent | Glutathione | 4 mM |
| VII | Salt | | |
| VIII | Stabilising agent | BSA | 0.2 mg/ml |
| IX | Detergent | Triton X-100 | 0.5% |
| X | Deoxynucleotide triphosphate | BrdUTP | 16 µM |
| XI | Primer | oligo dT | 80 ng/ml |
| XII | Protective agent | GTP | 0.5 mM |
| | Preservative | NaN$_3$ | 1.92 mM |
| Components in synovial fluid reverse transcriptase assay of the invention ||||
| I | Buffer | Hepes-HCl | 10 mM; pH 7.6 |
| II | Divalent metal ion | MnCl$_2$ | 1.2 mM |
| III | Chelator | EDTA | 0.13 mM |
| IV | Polyamine | Spermidine | 8 mM |
| V | RNase inhibitor | Dextran sulfate | 17 µg/ml |
| VI | Reducing agent | Glutathione | 0.3 mM |
| VII | Salt | KCl | 20 mM |
| VIII | Stabilising agent | BSA | 0.3 mg/ml |
| IX | Detergent | Triton X-100 | 0.5% |
| X | Deoxynucleotide triphosphate | BrdUTP | 16 µM |
| XI | Primer | oligo dT | 80 ng/ml |
| XII | Protective agent | GTP | 0.5 mM |
| | Preservative | NaN$_3$ | 1.92 mM |

TABLE 4

Components in the detection system

Washing buffer

| 3 mM | Tris-HCl, pH 8.6 |
|---|---|
| 0.01% | Tween-20 |
| 0.75% | Triton X-100 |

Buffer for anti-BrdUTP monoclonal antibody

| 25 mM | Bis-Tris propane pH 8.9 |
|---|---|
| 250 mg/ml | Non-fat dried milk |
| 0.01% | Tween-20 |
| 1% | Triton X-100 |
| 1.92 mM | NaN3 |

Alkaline phosphatase substrate solution

| 200 mM | Tris-HCl, pH 9.8 |
|---|---|
| 1 mM | MgCl$_2$ |
| 0.5 mg/ml | pNPP |
| 3.9 mM | NaN$_3$ |

TABLE 5

Correlation between RT enzyme concentration and OD values obtained with the Lenti RT assay from Cavidi Tech and the improved assay of the invention.

| pg/ml | Lenti RT assay from Cavidi Tech | Improved assay |
|---|---|---|
|  | 3 hr RT/30 min AP | 3 hr RT/30 min AP |
| 1240 | 1.274 | nd |
| 551 | 0.594 | nd |
| 245 | 0.332 | 9.999 |
| 109 | 0.175 | 1.837 |
| 48.4 | 0.108 | 0.989 |
| 21.5 | 0.070 | 0.525 |
| 9.6 | 0.052 | 0.264 |
| 4.25 | 0.046 | 0.174 |
| 1.89 | 0.054 | 0.121 |
| 0.839 | 0.041 | 0.101 |
| 0.373 | 0.042 | 0.091 |
| 0.166 | 0.040 | 0.081 |
| 0.074 | nd | 0.075 |
| 0.033 | nd | 0.075 |
| 0 | 0.042 | 0.078 |
|  | over night RT/2 hr AP | over night RT/2 hr AP |
| 1240 | 9.999 | nd |
| 551 | 9.999 | nd |
| 245 | 9.999 | 9.999 |
| 109 | 9.999 | 9.999 |
| 48.4 | 1.91 | 9.999 |
| 21.5 | 0.961 | 9.999 |
| 9.6 | 0.55 | 9.999 |
| 4.25 | 0.267 | 2.283 |
| 1.89 | 0.148 | 1.134 |
| 0.839 | 0.094 | 0.6 |
| 0.373 | 0.075 | 0.334 |
| 0.166 | 0.056 | 0.198 |
| 0.074 | nd | 0.144 |
| 0.033 | nd | 0.124 |
| 0 | 0.048 | 0.094 |
|  | over night RT/— over night AP | over night RT/— over night AP |
| 1240 | 9.999 | nd |
| 551 | 9.999 | nd |
| 245 | 9.999 | 9.999 |
| 109 | 9.999 | 9.999 |
| 48.4 | 9.999 | 9.999 |
| 21.5 | 9.999 | 9.999 |
| 9.6 | 9.999 | 9.999 |
| 4.25 | 2.217 | 9.999 |
| 1.89 | 1.155 | 9.999 |
| 0.839 | 0.595 | 9.999 |
| 0.373 | 0.403 | 2.289 |
| 0.166 | 0.191 | 1.171 |
| 0.074 | nd | 0.701 |
| 0.033 | nd | 0.577 |
| 0 | 0.115 | 0.251 | nd = not done

TABLE 6 k values obtained with the Lenti RT assay from Cavidi Tech and the improved Lenti RT assay of the invention

| Lenti RT assay from Cavidi Tech | | Improved assay | |
|---|---|---|---|
|  | k value |  | k value |
| 3 hr RT/30 min AP | 0.0012 | 3 hr RT/30 min AP | 0.0165 |
| over night RT/2 hr AP | 0.0432 | over night RT/2 hr AP | 0.5145 |
| over night RT/— over night AP | 0.5453 | over night RT/— over night AP | 5.2827 |

REFERENCES

Baltimore D. (1970) RNA-dependent DNA polymerase in virions of RNA tumour viruses. *Nature* 226:1209–1211.

Baltimore D, Smoler D (1971) Primer requirement and template specificity of the DNA polymerase of RNA tumor viruses. *PNAS* 68, 1507–11.

Barre-Sinoussi F, Chermann J C, Rey F, Nugeyre M T, Chamaret S, Gruest J, Dauguet C, Axler-Blin C, Vezinet-Brun F, Rouzioux C, Rozenbaum W, Montagnier L (1983). Isolation of a T-lymphotropic retrovirus from a patient at risk for acquired immune deficiency syndrome (AIDS). *Science* 220(4599):868–71.

Bird R E, Chang-Yeh A. (1996) Methods and kits for detecting viral transcriptase activity in a LD sample using an acidic pH or an elevated temperature. U.S. Pat. No. 5,817,457.

Di Cristofano A, Strazullo M, Longo L, La Mantia G (1995) Characterization and genomic mapping of the ZNF80 locus: expression of this zinc-finger gene is driven by a solitary LTR of ERV9 endogenous retroviral family. *Nucleic Acids Res* 23(15):2823–30.

Duvic M (1995) Human immunodeficiency virus and the skin: selected controversies. *J Invest Dermatol* 105(1 Suppl):117S–121S.

Eberle J., and R. Seibl. (1992) A new method for measuring reverse transcriptase activity by ELISA. *J. Virol. Methods* 40:347–356.

Ekstrand D. H. L., Awad R. J-K., Källander C. F. R. and Gronowitz J. S. (1996) A sensitive assay for the detection and quantification of RT activity, based on the use of carrier bound template and non-radioactive product detection, with special reference to HIV isolation. *Biotechnology and Applied Biochemistry.* 23, 95–105.

Faff O, Murray A B, Schmidt J, Leib-Mösch C, Erfle V, Hehlmann R, Thelen K, Löwer J, Kurth R (1992). Retrovirus-like particles from the human T47D cell line are related to mouse mammary tumour virus and are of human endogenous origin. *J Gen Virol* 73: 1087–97.

Ghosh S S, Musso G F (1987) Covalent attachment of oligonucleotides to solid supports. *Nucleic Acids Res* 15(13):5353–72.

Goff S. P. (1990) Retrovirus reverse transcriptase: Synthesis, Structure and Function. Review. *J.Acquir.Imm.Defic-.Syndr.* 3:817–31.

Gregorius K, Mouritsen S, Elsner H I (1995) Hydrocoating: a new method for coupling biomolecules to solid phases. *J Immunol Methods* 181(1):65–73.

Gronowitz J S., Neumüller M., Lennerstrand J., Bhikabahai R., Unge T., Weltman H & Källander C F R. (1991) Carrier bound templates for single tube reverse transcriptase assays and for combined purification and activity analyses, with special reference to HIV. *Biotech.Appl.Biochem* 13:127–142.

Gupta, P., Balachandran, Grovit, K., Webster, D., and Rinaldo. C. (1987) *J.Clin.Microbiol.* 25, 1122–1125.

Heneine W, Yamamoto S, Switzer W M, Spira T J, Folks T M. (1995) Detection of reverse transcriptase by a highly sensitive assay in sera from persons infected with human immunodeficiency virus type 1. *J Infect Dis* 171:1210–1216

Heneine W, Folks; Thomas M, Switzer W M, Yamamoto S. (1995) Methods for sensitive detection of reverse transcriptase. U.S. Pat. No. 5,849,494:

Jackson, B., Sannerud, K., Rhame, F., Tsang, R, and Balfour, H. H. (1987) *Diagn. Microbiol. Infect. Dis.* 7, 185–192.

Krieg A M, Steinberg A D (1990) Retroviruses and autoimmunity. *J Autoimmun.* 3(2):137–66

Krieg A M, Gourley M F, Perl A (1992) Endogenous retroviruses: potential etiologic agents in autoimmunity. FASEB J 6(8):2537–44.

Källander C F R, Gronowitz J S, Neumüller T M, Karlström R A, Langström-Persson U M. (1988). Method for polymerase activity determination. Svensk patent no 8804344-3, EP0447442B1.

Lee M., Sano K., Morales F. E., and D. T. Imagawa (1987) Sensitive reverse transcriptase assay to detect and quantitate human immunodeficiency virus. *J.Clin.Microbiol.* 25:1717–21.

Leib-Mösch C and Seifarth W (1996) Evolution and biological significance of human retroelements. Virus genes 11: 133–145.

Löwer R, Löwer J, Kurth R (1996) The viruses in all of us: characteristics and biological significance of human endogenous retrovirus sequences. Proc Natl Acad Sci USA 93(11):5177–84.

Martinelli S C, Goff S P (1990) Rapid reversion of a deletion mutation in Moloney murine leukemia virus by recombination with a closely related endogenous provirus. Virology 174(1):135–44.

Meese E, Gottert E, Zang K D, Sauter M, Schommer S, Mueller-Lantzsch N (1996) Human endogenous retroviral element k10(HERV-K10): chromosomal localization by somatic hybrid mapping and fluorescence in situ hybridization. Cytogenet Cell Genet 72(1):40–2.

Neumüller M., Karlström A. R, Källander C. F. R., and J. S. Gronowitz. (1990) Improved assays for DNA-polymerizing enzymes by the use of enzymatically synthetized 5-($^{125}$I)iodo-2'deoxyuridine triphosphate, illustrated by direct quantitation of anti-HIV reverse transcriptase antibody and by serum DNA polymerase analyses. *Biotech.Appl.Biocbem.* 12:34–56.

Niveleau A, Sage D, Reynaud C, Bruno C, Legastelois S, Thomas V, Dante R (1993) Covalent linking of haptens, proteins and nucleic acids to a modified polystyrene support. Immunol Methods 159(1–2):177–87.

Porstmann T., Meissner K., Glaser R., Döpel S-H., and G. Sydow. (1991) A sensitive non radioactive assay specific for HIV associated reverse transcriptase. *J.Virol.Meth.* 31:181–188.

Rasmussen S R, Larsen M R, Rasmussen S E (1991) Covalent immobilization of DNA onto polystyrene microwells: the molecules are only bound at the 5' end. Anal Biochem 198(i):138–42.

Silver 3, Maudru T, Fujita K and Repaske R. (1993) An RT-PCR assay for the enzyme activity of reverse transcriptase capable of detecting single virions. *Nucleic Acids Res* 21:3593–3594.

Temin H M, Mizutani S. (1970) RNA-dependent DNA polymerase in virions of Rous sarcoma virus. *Nature* 226:1211–1213.

Tönjes R R, Boller K, Limbach C, Lugert R, Kurth R. Characterization of human endogenous retrovirus type K virus-like particles generated from recombinant baculoviruses (1997) *Virology* 233(2):280–91.

Urabe T, Sano K, Nakano T, Odawara F, Lee MH, Otake T, et al. (1994) Differentiation between human immunodeficiency virus type 1 (HIV-1) and HIV-2 isolates by nonradioisotopic reverse transcriptase-typing assay. *J Clin Microbiol;* 32: 1870–75.

Urnovitz H B, and Murphy W H (1996) Human endogenous retroviruses: Nature, occurrence, and clinical implications in human disease. Clin Microbiol Rev 9: 72–99.

Weiss R: The search for human RNA tumor viruses. In R Weiss, N Teich, H Varmus, and J Coffin (eds) RNA Tumor viruses ($2^{nd}$ ed vol 1) 1205 1281. Cold Spring Harbor Laboratory Press, Cold Spring Harbor, N.Y., 1984.

Wilkinson D A Mager D L and Leong J-A (1994). Endogenous human retroviruses. In "The Retroviridae"(J A Levy, Ed), vol 3,pp 465–535.3 vols Plenum Press, New York.

Zammatteo N, Girardeaux C, Delforge D, Pireaux J J, Remacle J (1996) Amination of polystyrene microwells: application to the covalent grafting of DNA probes for hybridization assays. Anal Biochem 236(1):85–94.

Zinkernagel R M, Cooper S, Chambers J, Lazzarini R A, Hengartner H, Arnheiter H (1990) Virus-induced autoantibody response to a transgenic viral antigen. Nature 345: 68–71.

What is claimed is:

1. Reverse transcriptase (RT) assay kit comprising one or several package(s) containing solid phase bound polyriboadenylic acid (prA) and/or polydeoxyadenylic acid (pdA) template(s) produced by coupling prA and/or pdA to a polystyrene-based solid phase with a coupling solution consisting essentially of 1-methylimidazole, and prA and/or pdA at a pH≅ from about 5–7, followed by incubation, washing with a wash buffer, drying and packaging, RT-type adapted separately packaged assay components selected from the group consisting o a mixture of or separately a buffer, pH≅7–8, divalent metal ion, chelator, polyamine, RNase inhibitor, reducing agent, salt, stabilizing agent, and detergent, and a mixture of or separately lyophilized deoxynucleotide triphosphate, primer, protective agent and a concentrated washing buffer, and optionally lyophilized reference enzyme(s), and optionally components of a detection system comprising lyophilized alkaline phosphatase conjugated anti-BrdU monoclonal antibody, alkaline phosphatase substrate buffer and alkaline phosphatase substrate, and written instructions for use of the assay kit.

2. RT assay kit according to claim 1, wherein the solid phase is a microtiter plate and an aliquot of the coupling solution, which consists essentially of 100 mM 1-methylimidazole, pH≅5–7, and 0.5–2 mg/ml prA and/or pdA, is added to each well, followed by the incubation at a temperature of 10–60° C. for 0.5–10 h, and washing each well for the removal of the 1-methylimidazole with the wash buffer, which comprises Bis-Tris propane, pH≅5–7, and drying and packaging the plates.

3. RT assay kit according to claim 2, wherein 100 μl of the coupling solution, which consists essentially of 100 mM 1-methylimidazole, pH≅6.25, and 1 mg/ml prA and/or pdA, is added to each well, followed by the incubation at room temperature for ≅2 h, washing of each well with 2×300 μl of the wash buffer, which comprises 10 mM Bis-Tris propane, pH≅6.25, drying the plates at 37° C. for ≅25 minutes and putting the plates in foil bags and vacuum sealing the bags.

4. RT assay kit according to claim 1, wherein the assay components are one or a mixture of the buffers Tris and Hepes, pH≅7–8, one or a mixture of the divalent metal Ions $Mg^{2+}$ and $Mn^{2+}$, one or a mixture of the chelators ethylenediaminetetraacetic acid (EDTA) and ethylene glycol-bis(β-aminoethyl ether) N,N,N',N'-tetraacetic acid (EGTA) and, one or a mixture of the polyamines spermine and spermidine, one or a mixture of the RNase inhibitors heparin sulfate and dextran sulfate, one or a mixture of the reducing agents dithiothretiol (DTT), dithioerythritol (DTE), and glutathione, one or a mixture of the salts NaCl and KCl, one or a mixture of the stabilizing agents newborn calf serum (NCS) and bovine serum albumin (BSA), one or a mixture of the detergents Tween 20 and Triton X-100, the deoxynucleotide triphosphate BrdUTP, the primer oligo dT, and one or a mixture of the protective agent agents ATP, GTP and CTP.

5. Method of qualitative and quantitative analysis of RT activity in a biological sample comprising the steps of using and following the written instructions for the RT assay kit according to claim 1 for the determination of the RT activity in the biological sample.

6. Method according to claim 5 wherein the biological sample is selected from the group consisting of biological fluids and cell extracts.

7. Method according to claim 6 wherein the biological fluid is selected from the group consisting of plasma, serum, spinal fluid, synovial fluid and pleural fluid.

8. Method according to claim 5 followed by evaluation of the status of a RT activity related disorder or disease based on the result of the analysis of the RT activity.

9. A polystyrene-based solid phase support for a Reverse Transcriptase (RT) assay kit, wherein said polystyrene-based solid phase has coupled thereto polyriboadenylic acid (prA) and/or polydeoxyadenylic acid (pdA) template(s) by a coupling agent consisting essentially of 1-methylimidazole.

10. The solid phase support of claim 9, wherein the solid phase is a microtiter plate having wells and an aliquot of a coupling solution, which comprises 100 mM 1-methylimidazole, pH≅0.5–7, and 0.5–2 mg/ml prA and/or pdA, is added to each well, followed by the incubation at a temperature of 10–60° C. for 0.5–10 h, and washing each well for the removal of the 1-methylimidazole with the wash buffer, which comprises Bis-Tris propane, pH≅5–7, and drying and packaging the plates.

11. The solid phase support of claim 10, wherein 100 μl of the coupling solution, which consist essentially of 100 mM 1-methylimidazole, pH≅6.25, and 1 mg/ml prA and/or pdA, is added to each well, followed by the incubation at room temperature for ≅2 h, washing of each well with 2×300 μl of the wash buffer, which comprises 10 mM Bis-Tris propane, pH≅6.25, drying the plates at 37° C. for ≅25 minutes and putting the plates in foil bags and vacuum sealing the bags.

12. A method of making a solid phase support for a Reverse Transcriptase (RT) assay kit containing solid phase bound polyriboadenylic acid (prA) and/or polydeoxyadenylic acid (pdA) template(s) which comprises contacting a polystyrene-based solid phase with a coupling solution consisting essentially of 1-methylimidazole, and prA and/or pdA, followed by incubation, washing with a wash buffer and drying.

13. The method of claim 12, wherein the solid phase is a microtiter plate and an aliquot of the coupling solution, which comprises 100 mM 1-methylimidazole, pH≅5–7, and 0.5–2 mg/ml prA and/or pdA, is added to each well, followed by the incubation at a temperature of 10–60° C. for 0.5–10 h, and washing each well for the removal of the 1-methylimidazole with the wash buffer, which comprises Bis-Tris propane, pH≅0.5–7, and drying and packaging the plates.

14. The method of claim 13, wherein 100 μl of the coupling solution, which comprises 100 mM 1-methylimidazole, pH≅6.25, and 1 mg/ml prA and/or pdA, is added to each well, followed by the incubation at room temperature for a 2 h, washing of each well with 2×300 μl of the wash buffer, which comprises 10 mM Bis-Tris propane, pH≅6.25, drying the plates at 37° C. for ≅25 minutes and putting the plates in foil bags and vacuum sealing the bags.

\* \* \* \* \*